United States Patent
Vafi et al.

(10) Patent No.: US 6,988,899 B2
(45) Date of Patent: Jan. 24, 2006

(54) ELECTRONIC ASSEMBLY, AND APPARATUS AND METHOD FOR THE ASSEMBLY THEREOF

(75) Inventors: Habib Vafi, Brookfield, WI (US); Faisal Saeed, Waukesha, WI (US)

(73) Assignee: General Electric Company, Schenectady, NY (US)

( * ) Notice: Subject to any disclaimer, the term of this patent is extended or adjusted under 35 U.S.C. 154(b) by 0 days.

(21) Appl. No.: 10/709,175

(22) Filed: Apr. 19, 2004

(65) Prior Publication Data

US 2005/0233605 A1    Oct. 20, 2005

(51) Int. Cl.
*H01R 12/00*    (2006.01)

(52) U.S. Cl. .......................... 439/66; 439/74
(58) Field of Classification Search ............... 439/66, 439/74, 83, 71; 250/208, 338.4, 216, 370; 29/840; 430/321, 22; 324/755, 765; 257/461, 257/E21, 207, 916; 349/106; 345/46; 361/717
See application file for complete search history.

(56) References Cited

U.S. PATENT DOCUMENTS

| | | | | |
|---|---|---|---|---|
| 4,744,008 A | * | 5/1988 | Black et al. | 361/717 |
| 4,902,606 A | * | 2/1990 | Patraw | 430/314 |
| 5,075,201 A | * | 12/1991 | Koh | 430/321 |
| 5,145,552 A | * | 9/1992 | Yoshizawa et al. | 216/18 |
| 5,308,980 A | * | 5/1994 | Barton | 250/338.4 |
| 5,376,226 A | * | 12/1994 | Lau et al. | 216/18 |
| 5,696,377 A | * | 12/1997 | Kanzaki | 250/338.4 |
| 5,714,760 A | * | 2/1998 | Asatourian | 250/352 |
| 6,072,224 A | * | 6/2000 | Tyson et al. | 257/443 |
| 6,100,475 A | * | 8/2000 | Degani et al. | 174/264 |
| 6,107,619 A | * | 8/2000 | Cunningham et al. | 250/208.1 |
| 6,218,774 B1 | * | 4/2001 | Pope | 313/461 |
| 6,313,650 B1 | * | 11/2001 | Akram et al. | 324/754 |
| 6,417,514 B1 | * | 7/2002 | Eneim et al. | 250/352 |
| 6,496,162 B2 | * | 12/2002 | Kawakami et al. | 345/46 |
| 6,707,046 B2 | | 3/2004 | Possin et al. | 250/370.11 |
| 6,710,612 B2 | * | 3/2004 | Farnworth et al. | 324/755 |

FOREIGN PATENT DOCUMENTS

| | | |
|---|---|---|
| EP | 1 120 833 A | 8/2001 |
| FR | 2 758 655 A | 7/1998 |

* cited by examiner

*Primary Examiner*—Alexander Gilman
(74) *Attorney, Agent, or Firm*—Cantor Colburn LLP

(57) ABSTRACT

An electronic assembly having a first layer and a second layer is disclosed. The first layer has a first interface surface and a plurality of cavities formed in the first interface surface. The second layer has a second interface surface and a plurality of projections disposed at the second interface surface, where the plurality of projections are aligned with and disposed at the plurality of cavities. An electrically conductive connecting material is disposed at the plurality of cavities such that the connecting material connects the plurality of projections to the respective plurality of cavities.

14 Claims, 2 Drawing Sheets

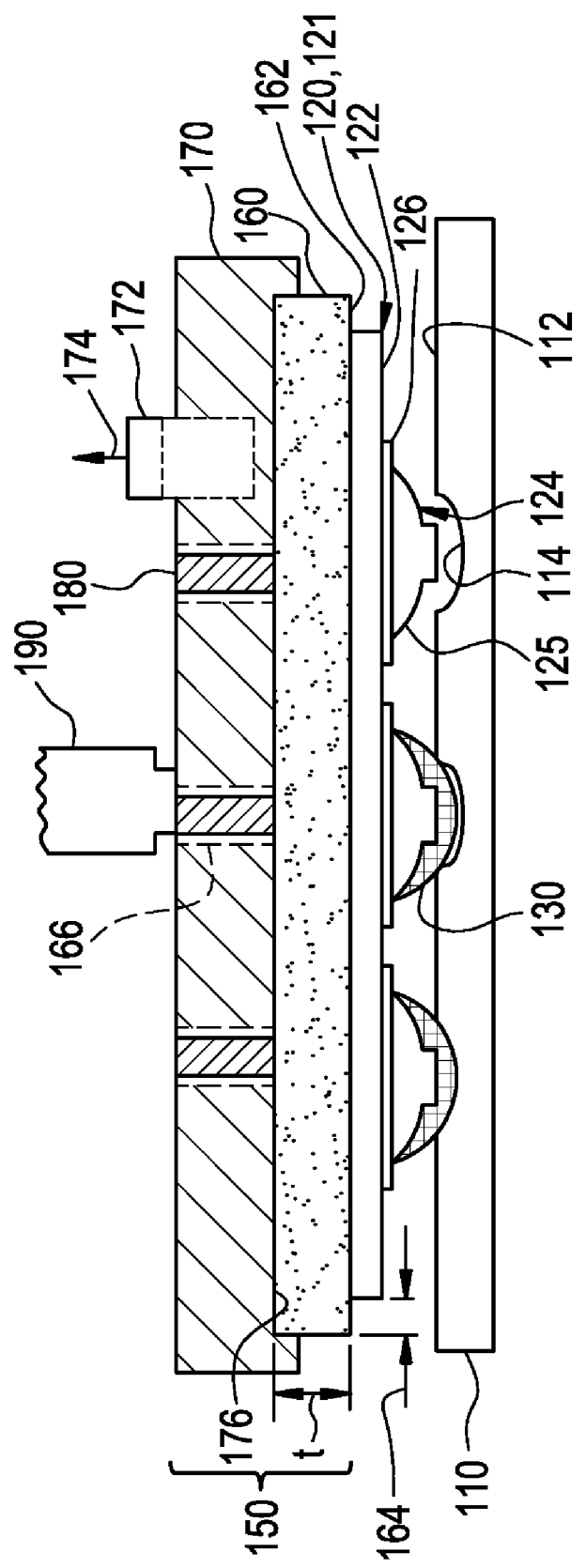

ELECTRONIC ASSEMBLY, AND APPARATUS AND METHOD FOR THE ASSEMBLY THEREOF

BACKGROUND OF THE INVENTION

The present disclosure relates generally to an electronic assembly and to the apparatus and method for assembling the electronic assembly, and particularly to an apparatus and method for assembling a light detector for use in medical diagnostic equipment.

A type of detector array used for computed tomography is made from a silicon wafer having a diode array that is positioned on a ceramic substrate, such as Aluminum Nitride or AlN for example. The silicon diode-array wafer is connected, by means of stud-bump arrays, to metal pads on the ceramic substrate. The connection method may involve bonding via a metal-filled adhesive, such as silver-filled epoxy for example, or by soldering. For backlit photodiode arrangements, the silicon wafer for the diode array needs to be thin, so as to minimize the adverse effects on the X-ray beam that is converted into visible light via a scintillator for detection by the diode array. The thinner the silicon diode-array wafer is, the less attenuation and scattering there will be of the X-ray beam, however, the more susceptible the wafer will be to physical damage. Additionally, for high resolution imaging, it is desirable to have a silicon diode-array wafer that has a high density of photodiodes; however, such high density may require a high degree of control in the manufacturing of such detectors. While some advances have been made in the assembly of detector arrays for use in computed tomography, such as the use of vacuum suction cups to pick and place the diode array wafers, there is still a need in the art for a detector array arrangement, and a method and apparatus for assembling the detector array arrangement, that overcomes these drawbacks.

BRIEF DESCRIPTION OF THE INVENTION

Embodiments of the invention include an electronic assembly having a first layer and a second layer. The first layer has a first interface surface and a plurality of cavities formed in the first interface surface. The second layer has a second interface surface and a plurality of projections disposed at the second interface surface, where the plurality of projections are aligned with and disposed at the plurality of cavities. An electrically conductive connecting material is disposed at the plurality of cavities such that the connecting material connects the plurality of projections to the respective plurality of cavities.

Other embodiments of the invention include an apparatus for assembling an electronic assembly having a top layer. The apparatus includes a porous rigid element having a thickness and a support surface, and a housing configured to hold the porous rigid element and to provide a positive vacuum to the porous rigid element, wherein the applied positive vacuum results in a positive vacuum at the support surface for picking up the top layer.

Further embodiments of the invention include a method for assembling an electronic assembly, the assembly including a first layer having a first interface surface and a plurality of cavities formed in the first interface surface, and a second layer having a second interface surface and a plurality of projections disposed at the second interface surface. The first layer is positioned and the second layer is vacuum held via an apparatus such that the first and the second interface surfaces oppose each other. The plurality of projections are aligned and engaged with the plurality of cavities, and the vacuum hold is sufficiently reduced so as to release the second layer.

BRIEF DESCRIPTION OF THE DRAWINGS

Referring to the exemplary drawings wherein like elements are numbered alike in the accompanying Figures:

FIG. 4 depicts an exemplary apparatus for assembling the assemblies depicted in FIGS. 1–3.

DETAILED DESCRIPTION OF THE INVENTION

An embodiment of the invention provides a light detector for use in medical diagnostic equipment, such as computed tomography for example, having an array of backlit photodiodes electrically bonded to a ceramic substrate having copper runs for signal communication. At the bonding interface, the diode arrays have elongated electrical connections, or stud bumps as they are referred to, that extend into cavities formed in the ceramic substrate, which provide pockets for constraining the conductive epoxy or solder from electrically shorting out adjacent diodes. An alternative embodiment of the invention provides an apparatus for vacuum holding the photodiode array while assembling the same onto the ceramic substrate. A further embodiment of the invention provides a method for using the assembly apparatus for assembling the light detector. While embodiments described herein depict an array of backlit photodiodes assembled to a ceramic substrate as an exemplary electronic assembly, it will be appreciated that the disclosed invention is also applicable to other electronic assemblies, such as processing chips on a printed circuit board for example.

Figure 1:
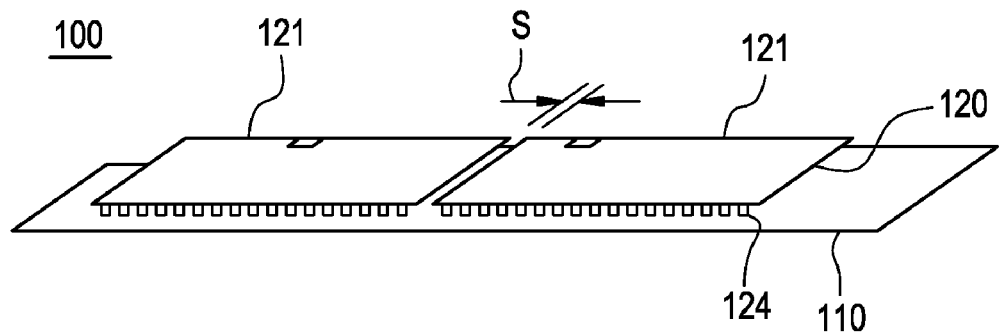
FIG. 1 depicts an isometric view of an exemplary assembly for practicing embodiments of the invention.
Figure 2:
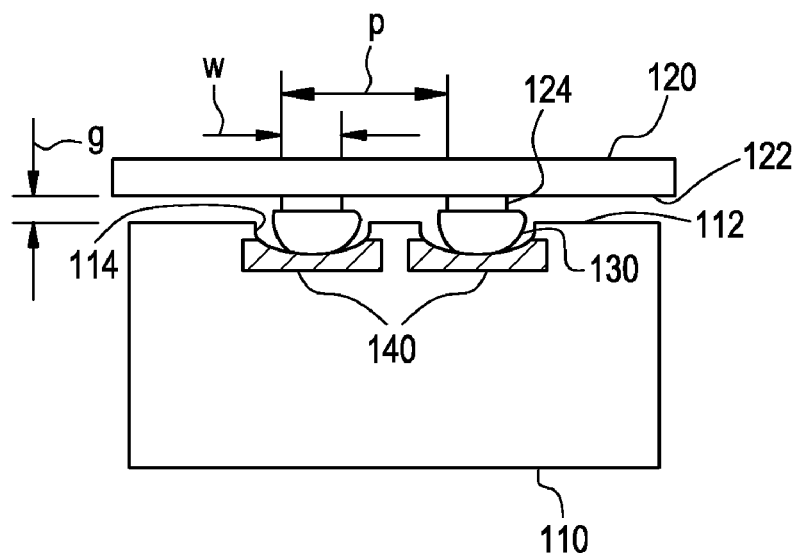
FIG. 2 depicts a cross section side view of an expanded portion of the assembly of FIG. 1.
Figure 3:
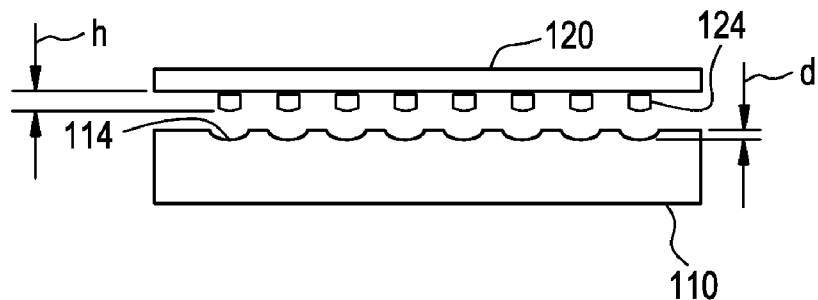
FIG. 3 depicts a similar view to that of FIG. 2, but prior to the assembly of the respective parts.

FIGS. 1–3 depict an exemplary embodiment of an electronic assembly 100 having a first layer 110 and a second layer 120. FIG. 1 depicts an isometric perspective of electronic assembly 100, FIG. 2 depicts a side view of a portion of the assembly of FIG. 1 subsequent to assembling, and FIG. 3 depicts a side view of the assembly of FIG. 1 prior to assembling. First layer 110 includes a first interface surface 112 having a plurality of cavities 114 formed therein, and second layer 120 includes a second interface surface 122 having a plurality of projections 124 disposed thereat. In an embodiment, second layer 120 includes a diode array having a plurality of backlit photodiodes 121 in electrical communication with projections 124. During the assembly of second layer 120 onto first layer 110, projections 124 are aligned with and assembled into cavities 114. In an embodiment, the ends of projections 124 are shaped to mirror the shape of the interior surface of cavities 114, which may be spherical in shape for example. Projections 124 are electrically bonded to cavities 114 via an electrically conductive connecting material 130, which may be conductive epoxy or solder for example. Prior to assembly, connecting material 130 may be applied to projections 124 or cavities 114, and in the assembled state is referred to as being disposed at cavities 114. By introducing cavities 114 at first interface surface 112 of first layer 110, connecting material 130 will naturally be constrained by the pocket shape of cavities 114 during the curing of connecting material 130, which may involve the heating of an epoxy or the heating and cooling of a solder, via a reflow and solidification process. Copper conductors 140 at first layer 110 are exposed via an etching process that creates cavities 114, thereby providing a point of electrical contact for connecting material 130 to bond to, which in turn provides an electrical communication path from second layer 120 (a backlit photodiode array for example), to first layer 110 (a ceramic substrate having wire runs for example), and ultimately to readout electronics (not shown) for the diode signals. Copper conductors 140, also referred to as runs, may have layers of nickel and gold plated thereon after cavities 114 are formed, thereby protecting the copper pads at cavities 114 from oxidation. As a result of an etching process to create cavities 114, copper conductors 140 may have a nominal thickness that is reduced slightly at the site of cavities 114.

Cavities 114 are formed having a depth d with respect to first interface surface 112, and in the assembled state first interface surface 112 is disposed apart from second interface surface 122 by a gap g, depicted in FIGS. 2 and 3. Accordingly, projections 124 have a length h that is equal to or less than the sum of depth d and gap g. If length h is less than the sum of depth d and gap g, such as may be the case under normal tolerance conditions, then connecting material 130 will bridge the gap.

Projections 124 have a width, or alternatively a diameter, w and are arranged with a pitch p. In an embodiment, projections 124 have a width w equal to or greater than about 100 microns (micrometers) and equal to or less than about 700 microns. In an alternative embodiment, projections 124 have a width w equal to about 500 microns. In an embodiment, projections 124 have a pitch p equal to or greater than about 1.1 times width w and equal to or less than about 3 times width w. In an alternative embodiment, projections 124 have a pitch p equal to about 2 times width w.

In an embodiment, and by appropriately sizing width w and pitch p, the plurality of photodiodes 121 in photodiode array 120, depicted in FIG. 1, may be spaced on first layer 110 with an edge spacing s equal to or less than about 100 microns. In an alternative embodiment, edge spacing s is equal to or less than about 25 microns, and in a further embodiment, edge spacing s is equal to about 10 microns. The close spacing between the photodiodes 121 of photodiode array 120 is made possible at least in part by cavities 114 constraining connecting material 130 so that adjacent photodiodes 121 are not electrically shorted.

Referring now to FIG. 4, an apparatus 150 for assembling electronic assembly 100 is depicted in cross section view. In electronic assembly 100, second layer 120 is also herein referred to as a photodiode array or a top layer, where top layer may be just one photodiode 121 of photodiode array 120. Apparatus 150 includes a porous rigid element 160 having a thickness t and a support surface 162, and a housing 170 configured to hold porous element 160 and to provide a positive vacuum to porous element 160 via a vacuum port 172. By applying a vacuum in the direction of arrow 174, a positive vacuum results at the exposed surfaces of porous element 160, and particularly at support surface 162, which is used for holding or picking up top layer 121. In an embodiment, housing 170 includes a pocket 176 with sides disposed around all sides of porous element 160 except support surface 162, thereby leaving a portion of the thickness of porous element 160 exposed and directing the positive vacuum at porous element 160 toward support surface 162.

In an embodiment, support surface 162 is fabricated to have a flatness equal to or less than about 20 microns, that is, support surface 162 defines a theoretical surface that does not vary from a planar surface, which contacts the theoretical surface at three or more points, by more than 20 microns over the expanse of support surface 162. In an alternative embodiment, support surface 162 is fabricated to have a flatness equal to or less than about 10 microns. Porous element 160 may be fabricated with the desired flatness at support surface 162 with or without secondary machining.

As depicted in FIG. 4, support surface 162 may have an overall dimension that is substantially matched to the corresponding overall dimension of photodiode 121, as evidenced by only a slight overhang 164 at the edge of porous element 160. While the cross section view of FIG. 4 shows only one overall dimension of support surface 162 being substantially matched to the corresponding overall dimension of photodiode 121, namely that overall dimension in the plane of the paper, it will be appreciated that a second overall dimension of support surface 162 may also be substantially matched to that corresponding overall dimension of photodiode 121, namely the overall dimension perpendicular to the plane of the paper.

Porous element 160 may include a plurality of cavities 166 having disposed therein a plurality of heater elements 180 for processing connecting material 130 so as to adhere the projections 124 to cavities 114. In an embodiment, the processing of connecting material 130 involves heating electrically conductive epoxy to cure and solidify the epoxy. In an alternative embodiment, the processing of connecting material 130 involves heating solder to cause a solder re-flow that solidifies on cooling. Heating elements 180 are in signal communication with a control unit (not shown) for controlled heating during assembly. The control unit also controls the presence and absence of a vacuum at vacuum port 172, and the action of control arm 190 that is in operable communication with apparatus 150 for controlling the location of apparatus 150 during assembly. The control unit may be any type of control unit suitable for the purposes disclosed herein.

Since photodiodes 121 may be manufactured with a less than desirable flatness, apparatus 150 is configured such that the combination of support surface 162 and resultant positive vacuum at support surface 162 is sufficient to flatten photodiode 121, having an original flatness equal to or greater than about 50 microns and a typical thickness equal to about 100 microns, to a final flatness equal to or less than about 20 microns. In an alternative embodiment, the combination of support surface 162 and resultant positive vacuum at support surface 162 is sufficient to flatten photodiode 121, having an original flatness equal to or greater than about 100 microns, to a final flatness equal to or less than about 10 microns.

In view of the foregoing, a method of assembling electronic assembly 100 using apparatus 150 includes: positioning first layer at an assembly station (not shown); vacuum holding second layer 120, 121 via apparatus 150 such that first and second interface surfaces 112, 122 oppose each other; aligning plurality of projections 124 with plurality of cavities 114; engaging plurality of projections 124 with plurality of cavities 114; and, sufficiently reducing the vacuum hold at support surface 162 so as to release second layer 121 from apparatus 150. An electrically conductive connecting material 130 may be applied to the plurality of cavities 114 or to the plurality of projections 124 prior to engaging projections 124 with cavities 114. Subsequent to the engaging action, the connecting material 130 is processed in the manner discussed previously so as to adhere projections 124 to cavities 114. In an embodiment, the vacuum hold may be maintained for a sufficient amount of time to allow connecting material 130 to at least partially cure enough to keep photodiode 121 in a firm position.

The method disclosed herein may enable accurate placement of photodiodes 121 to within a sidewise tolerance of about 10 microns, and to a parallel tolerance, with respect to the ceramic substrate 110, of about 30 microns.

In an alternative embodiment, and with reference to FIGS. 2 and 4, projections 124 may be of uniform thickness, as depicted in FIG. 2, or of non-uniform thickness, as depicted in FIG. 4. Where projections 124 are non-uniform in thickness, a wide base 125 may be utilized with a conductive pad 126 for improved signal communication between photodiode 121 and first layer 110.

As disclosed, some embodiments of the invention may include some of the following advantages: a high packing density of photodiodes on the ceramic substrate with a small spacing therebetween; effective containment of the conductive connecting material to prevent shorting between adjacent diodes; stud bumps of a photodiode having a small pitch with respect to the dimension of the photodiode; ability to flatten the photodiode during assembly by using a pick-and-place apparatus having a vacuum across the support surface; and, use of heater elements integral with the assembly apparatus for enhanced productivity in curing the epoxy or solder.

While the invention has been described with reference to exemplary embodiments, it will be understood by those skilled in the art that various changes may be made and equivalents may be substituted for elements thereof without departing from the scope of the invention. In addition, many modifications may be made to adapt a particular situation or material to the teachings of the invention without departing from the essential scope thereof. Therefore, it is intended that the invention not be limited to the particular embodiment disclosed as the best or only mode contemplated for carrying out this invention, but that the invention will include all embodiments falling within the scope of the appended claims. Moreover, the use of the terms first, second, etc. do not denote any order or importance, but rather the terms first, second, etc. are used to distinguish one element from another. Furthermore, the use of the terms a, an, etc. do not denote a limitation of quantity, but rather denote the presence of at least one of the referenced item.

What is claimed is:

1. An electronic assembly comprising:
a first layer having a first interface surface and a plurality of cavities formed in the first interface surface;
a second layer having a second interface surface and a plurality of electrically conductive projections disposed at the second interface surface, wherein the plurality of projections are aligned with and disposed at the plurality of cavities, the second layer comprising a diode array having a plurality of backlit photodiodes in electrical communication with the plurality of projections; and
an electrically conductive connecting material disposed at the plurality of cavities such that the connecting material non-separably connects the plurality of projections to the respective plurality of cavities, each of the plurality of cavities being configured to constrain the connecting material disposed thereat from outward flow;
wherein the plurality of cavities are formed having a depth d in the first interface surface;
wherein the first interface surface is disposed apart from the second interface surface by a gap g; and
wherein the plurality of projections have a length h that is equal to or less than the sum of the depth d and the gap g, such that the connecting material bridges the distance defined by (d+g−h).

2. The assembly of claim 1, wherein:
the plurality of projections are shaped to mirror the shape of the plurality of cavities.

3. The assembly of claim 1, wherein adjacent projections are absent direct electrical communication.

4. The assembly of claim 1, wherein:
the plurality of projections have a width w equal to or greater than about 100 microns and equal to or less than about 700 microns.

5. The assembly of claim 4, wherein:
the plurality of projections have a width w equal to about 500 microns.

6. The assembly of claim 4, wherein:
the pitch of the plurality of projections is equal to or greater than about 1.1 times the width w and equal to or less than about 3 times the width w.

7. The assembly of claim 6, wherein:
the pitch of the plurality of projections is equal to about 2 times the width w.

8. The assembly of claim 1, wherein:
the first layer comprises a ceramic substrate; and
the connecting material comprises a conductive epoxy, a conductive solder, or any combination comprising at least one of the foregoing materials.

9. The assembly of claim 8, wherein:
the assembly comprises a light detector for use in medical diagnostic equipment.

10. The assembly of claim 8, wherein:
the plurality of photodiodes are spaced on the first layer with an edge spacing equal to or less than about 100 micrometers.

11. The assembly of claim 10, wherein:
the plurality of photodiodes are spaced on the first layer with an edge spacing equal to or less than about 25 micrometers.

12. The assembly of claim 11, wherein:
the plurality of photodiodes are spaced on the first layer with an edge spacing equal to about 10 micrometers.

13. An electronic assembly comprising:
a first layer having a plurality of pockets;
a second layer comprising a diode array having a plurality of backlit photodiodes having a plurality of electrically conductive projections, wherein the plurality of projections are aligned with and disposed at the plurality of pockets with a defined distance therebetween; and
an electrically conductive connecting material disposed at the plurality of pockets such that the plurality of projections are electrically and non-separably bonded to the respective plurality of pockets via the electrically conductive connecting material;
wherein the conductive connecting material bridges the defined distance; and
wherein each of the plurality of pockets are configured to constrain the connecting material disposed thereat from outward flow.

14. A multi-layer backlit photodiode array electronic assembly, comprising:
a first layer having a plurality of pockets formed in a first interface surface;
a second layer having a plurality of electrically conductive projections disposed at a second interface surface, wherein the plurality of projections are aligned with and disposed at the plurality of cavities, and wherein the plurality of projections and the plurality of pockets are spaced apart by a defined distance; and an electrically conductive connecting material disposed between the plurality of pockets and the plurality of projections such that the connecting material bridges the defined distance and non-separably connects the plurality of projections to the plurality of pockets, each of the plurality of pockets being configured to constrain the connecting material disposed thereat from outward flow;

wherein the second layer comprises the backlit photodiode array.

* * * * *